United States Patent
Umezawa et al.

(10) Patent No.: US 6,924,119 B2
(45) Date of Patent: Aug. 2, 2005

(54) CGMP-VISUALIZING PROBE AND A METHOD OF DETECTING AND QUANTIFYING OF CGMP BY USING THE SAME

(75) Inventors: Yoshio Umezawa, Tokyo (JP); Moritoshi Sato, Tokyo (JP); Takeaki Ozawa, Chiba (JP)

(73) Assignee: Japan Science and Technology Corporation, Saitama (JP)

( * ) Notice: Subject to any disclaimer, the term of this patent is extended or adjusted under 35 U.S.C. 154(b) by 208 days.

(21) Appl. No.: 10/070,131

(22) PCT Filed: Jun. 29, 2001

(86) PCT No.: PCT/JP01/05631

§ 371 (c)(1),
(2), (4) Date: Apr. 1, 2002

(87) PCT Pub. No.: WO02/03069

PCT Pub. Date: Jan. 10, 2002

(65) Prior Publication Data

US 2002/0137115 A1 Sep. 26, 2002

(30) Foreign Application Priority Data

Jul. 4, 2000 (JP) ........................................ 2000-202730

(51) Int. Cl.[7] .............................. C12N 9/12; C12Q 1/48; G01N 33/52; G01N 33/566; G01N 33/58
(52) U.S. Cl. ........................ 435/15; 435/194; 530/350; 436/94; 436/501
(58) Field of Search .................... 435/194, 15; 530/350; 436/94, 501

(56) References Cited

U.S. PATENT DOCUMENTS 5,998,204 A   12/1999   Tsien et al. ................. 435/325

OTHER PUBLICATIONS

J. Zhao et al. "Progressive Cyclic Nucleotide–induced Conformational Changes in the cGMP–dependent Protein Kinase Studie by Small Angle X–ray Scattering in Solution", J. Biol. Chem. 272(50):31929–31936. (Dec. 1997).*

Norbert Wild et al., "Expression of a chimeric cGMP–sensitive regulatory subunit of the cAMP–dependent protein kinase type Iα", FEBS Letters, 374, 1995, pp. 356–362.

Kazuhiko Seya et al., "A Fluorometric Assay for Cyclic Guanosine 3', 5'–Monophosphate Incorporating a Sep–Pak Cartridge and Enzymatic Cycling", Analytical Biochemistry, 272, 1999, pp. 243–249.

Moritoshi Sato et al., "Fluorescent Indicators for Cyclic GMP Based on Cyclic GMP–Dependent Protein Kinase Iα and Green Fluorescent Proteins", Analytical Chemistry, Dec. 15, 2000, 72, pp. 5918–5924.

Akira Honda et al., "Spatiotemporal dynamics of guanosine 3', 5'–cyclic monophosphate revealed by a genetically encoded, fluorescent indicator", PNAS, Feb. 27, 2001, 98, pp. 2437–2442.

* cited by examiner

Primary Examiner—Rebecca Prouty
(74) Attorney, Agent, or Firm—Wenderoth, Lind & Ponack, L.L.P.

(57) ABSTRACT

As a cGMP-visualizing probe capable of detecting and quantifying cGMP easily and accurately even in vivo and for a method of detecting and quantifying cGMP by using the same, a cGMP-visualizing probe comprising a polypeptide, which binds specifically to cGMP, and two chromophores having different fluorescence wavelengths each linked respectively to the two terminals of said polypeptide is provided.

3 Claims, 8 Drawing Sheets

Fig. 8

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Synthesized Oligopeptide
```

```
<400> SEQUENCE: 1

Met Asp Glu Leu Lys Tyr
1               5

<210> SEQ ID NO 2
<211> LENGTH: 10
<212> TYPE: PRT
<213> ORGANISM: Artificial Sequence
<220> FEATURE:
<223> OTHER INFORMATION: Synthesized Oligopeptide

<400> SEQUENCE: 2

Tyr Pro Tyr Asp Val Pro Asp Tyr Ala Asn
1               5                   10
```

CGMP-VISUALIZING PROBE AND A METHOD OF DETECTING AND QUANTIFYING OF CGMP BY USING THE SAME

This application is a 371 of PCT/JP01/05631 filed Jun. 29, 2001.

TECHNICAL FIELD

The invention of the present application relates to a visualizing probe for detecting and quantifying cGMP and a method of detecting and quantifying cGMP by using the same. More specifically, the present invention relates to a cGMP-visualizing probe which can specifically bind to cGMP, thereby generating an optical change to enable detection and quantification of cGMP, and a method of detecting and quantifying cGMP by using the same.

BACKGROUND ART

Cyclic guanosine monophosphate (cGMP) is an intracellular second messenger which acts as a signal molecule in various biochemical reaction processes in living body. So far it has been revealed that various physiological processes such as relaxation of vascular muscle cells, phototransduction in retina, epithelial electrolyte transport, bone growth, and neuronal activity are regulated by cGMP. Accordingly, if the synthesis, decomposition and localization of cGMP in living cells can be clarified, not only would the mechanism of cGMP at the cellular and tissue levels in the circulatory system, in the kidney and retina, in the olfactory and central nerves be understood, but would also provide hints for obtaining knowlege on substances such as phosphodiesterase inhibitors, which control intracellular cGMP levels in the cell.

Conventional methods of detecting and quantifying cGMP include radioimmunoassays using a radioisotope-labeled compound. However, this method involves disrupting cells and detecting the binding of cellular lysates to the labeled compound to analyze total cGMP levels, and did not realize the accuracy required in cell-biology and pharmaceutics.

Further, since such radioimmunoassay is a destructive measurement method, and further because the radioisotope-labeled compound is poor in stability and requires caution in handling, such conventional method could only be applied only to in vitro measurement of cGMP; in this respect, there was a limit to which the method could be applied.

The invention of the present application has been made in view of the circumstances as described above, and the object of the present invention is to solve the problem in the prior art and to provide a cGMP-visualizing probe, which enables the easy and highly accurate detection and quantification of cGMP, even in vivo, as well as a method of detecting and quantifying cGMP by using the same.

DISCLOSURE OF INVENTION

To solve the problem described above, the invention of the present application first provides a cGMP-visualizing probe, comprising a polypeptide that binds specifically to cGMP and two chromophores with different fluorescence wavelengths, which are each linked to the two terminals of the polypeptide.

Secondly, the invention of the present application provides the cGMP-visualizing probe, wherein the polypeptide that binds specifically to cGMP is a cGMP-binding protein.

Thirdly, the invention of the present application provides the cGMP-visualizing probe, wherein the polypeptide that binds specifically to cGMP is cGMP-dependent kinase Iα.

Fourthly, the invention of the present application provides the cGMP-visualizing probe, wherein the chromophores are cyan fluorescent protein linked to the N-terminal of the polypeptide and yellow fluorescent protein linked to the C-terminal of the polypeptide.

Fifthly, the invention of the present application provides a method for detecting and quantifying cGMP. which comprises making the cGMP-visualizing probe coexist with cGMP; and measuring the change in the fluorescence wavelength.

Sixthly, the invention of the present application provides the method for detecting and quantifying cGMP, which comprises introducing a polynucleotide expressing the cGMP-visualizing probe into cells, thereby making the cGMP-visualizing probe coexist with cGMP.

Seventhly, the invention of the present application provides the method for detecting and quantifying cGMP, which comprises introducing a polynucleotide expressing a cGMP-visualizing probe into cells and performing ontogenesis from the non-human animal totipotent cells, thereby making the cGMP-visualizing probe coexist with cGMP in every cell of the resultant animal or its offspring.

Eighthly, the invention of the present application provides a non-human animal or offspring thereof, which is obtained by introducing a polynucleotide expressing a cGMP-visualizing probe into cells and performing ontogenisis from the non-human animal totipotent cells.

Ninthly, the invention of the present application provides a method for screening a substance, which comprises introducing a test sample containing the substance into a non-human animal or offspring thereof, and quantifying cGMP in the cells of the non-human animal or offspring thereof.

BEST MODE FOR CARRYING OUT THE INVENTION

The cGMP-visualizing probe of the invention of the present application comprises two sites each having a different function. That is, this cGMP-visualizing probe comprises a site that selectively recognizes cGMP and binds specifically to cGMP, and coloring sites that transmit optical signals upon recognition of cGMP by the site that binds specifically to cGMP.

The detection and quantifcation of cGMP is enabled when the cGMP-visualizing probe of this invention coexists with cGMP; the site that binds specifically to cGMP (cGMP-binding site) binds to cGMP, causing the change of configuration of the coloring sites, which may be detected as an optical change.

The site for binding specifically to cGMP is, for example a polypeptide such as various cGMP-binding proteins. The cGMP-binding proteins include cGMP-dependent protein kinase Iα (PKG Iα).

Figure 1:
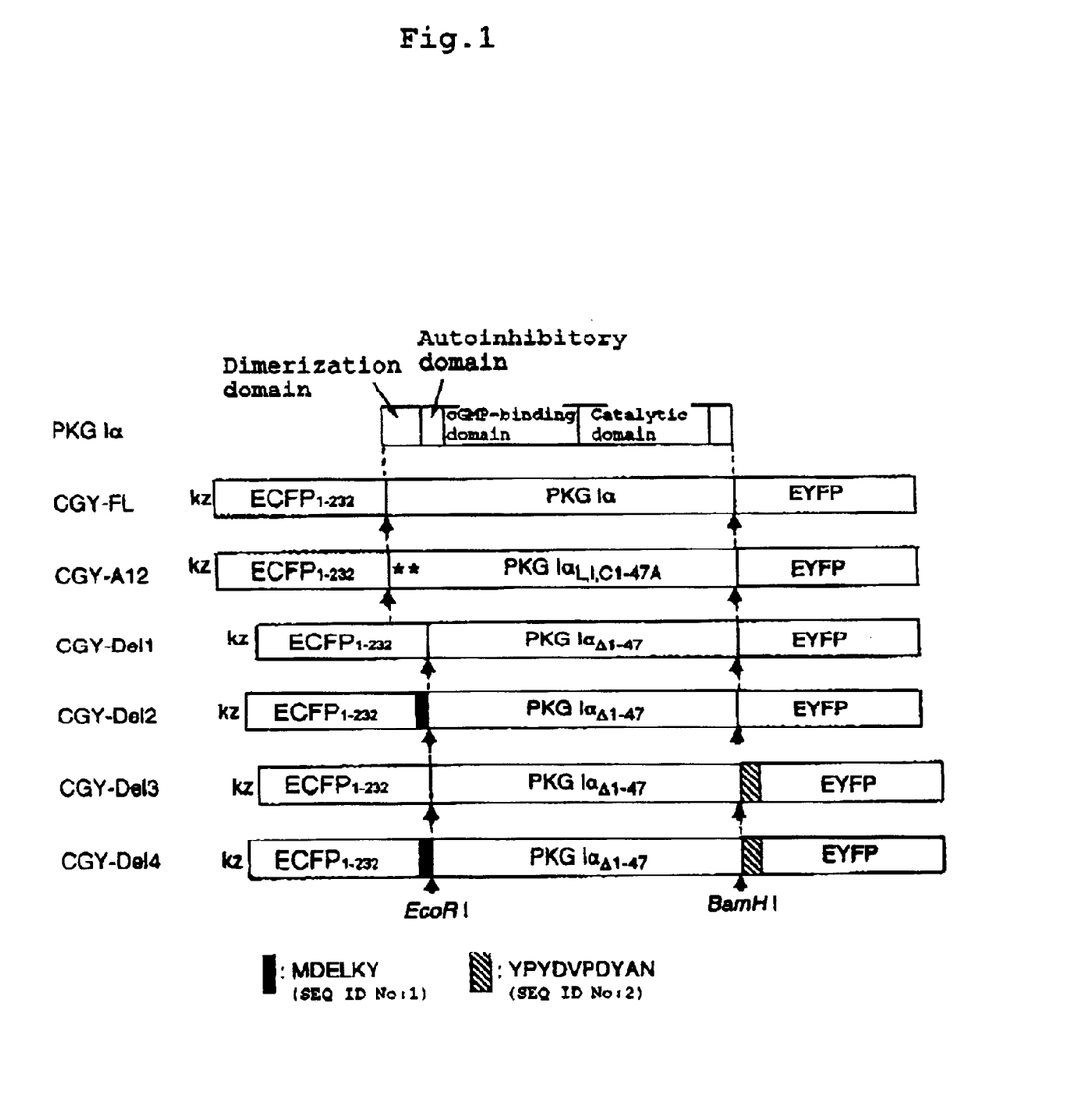
FIG. 1 is a schematic representations of the structures of the cGMP-visualizing probe of the present invention.

Mammalian PKG Iα is composed of two identical monomers each having four types of functional domains (dimerization domain, autoinhibitory domain, cGMP-binding domain and catalytic domain) as shown in FIG. 1. The dimerization domain located at the N-terminus is composed of a leucine/isoleucine zipper motif. In the absence of cGMP, PKG Iα displays a kinase inactive closed conformation, in which its catalytic center is occupied by an autoinhibitory domain. Upon binding of PKG Iα to cGMP, PKG Iα displays an open conformation in which the autoinhibitory domain is removed from the catalytic center. Accordingly, if chromophores are linked to both terminals of PKG Iα, an optical change will occur upon binding of PKG Iα to cGMP, thus allowing the optical detection of the binding to cGMP.

As a matter of course, the polypeptide binding specifically to cGMP is not limited to PKG Iα or cGMP-binding proteins, and every possible synthetic or natural peptide chain may be used.

In the cGMP-visualizing probe of the invention of the present application, the site transducing the molecular recognition to an optical change may be chosen from various chromophores. In this transduction, the chromophores should generate a change in wavelength highly accurately by responding to the change in the stereostructure resulting from the binding of the cGMP-binding site to cGMP. In the field of biochemistry, there are a wide variety of generally used fluorescent chromophores including, as chromophores responding rapidly to a change in the stereostructure, those causing change in color by the generation of fluorescence resonance energy transfer (FRET).

As the sites transducing the molecular recognition event to an optical change in the cGMP-visualizing probe of the invention of the present application, two fluorescent chromophores each having a different fluorescence wavelength are linked respectively to the two terminals of the polypeptide binding specifically to cGMP. As such fluorescent chromophores, cyan fluorescent protein (CFP) i.e. a blue-shifted mutant of green fluorescent protein (GFP) and yellow fluorescent protein (YFP) i.e. a red-shifted mutant of GFP are preferably selected. By linking CFP to the N-terminal of the polypeptide binding specifically to cGMP and YFP to the C-terminal thereof, the two act, respectively as donor and acceptor to generate FRET.

That is, when the cGMP-visualizing probe of the invention of the present application coexists with cGMP, the cGMP-binding protein binds to cGMP to allow FRET to be generated by the fluorescent chromophores at the N- and C-terminals thereof, thus causing a change in fluorescence wavelength. Then, cGMP may be detected by measuring such fluorescence change by a variety of conventional chemical and/or biochemical analysis techniques. Further, the concentration of cGMP in a sample solution may also be quantified by previously calibrating the relationship between fluorescence intensity and cGMP concentration.

In the invention of the present application, various methods are applicable for the cGMP-visualizing probe described above to coexist with cGMP. For example, a method wherein cells are disrupted, cGMP is eluted from the cells, and the cGMP-visualizing probe is added to the solution, to allow the cGMP-visualizing probe to be coexistent with cGMP maybe applied. When the cGMP-visualizing probe is allowed to be coexistent with cGMP by such a method, cGMP can be detected and quantified in vitro.

In the present invention, by introducing an expression vector having the cGMP-visualizing probe integrated therein into individual cultured cells, the cGMP-visualizing probe may also be made to coexist with cGMP. For such a method, the expression vector, a plasmid vector for expression in animal cells is preferable. The introduction of such plasmid vectors into cells, may be accomplished by known methods such as electroporation, calcium phosphate method, liposome method and DEAE-dextran method. By using the method of introducing an expression vector having the cGMP-visualizing probe integrated therein into cells, cGMP and the cGMP-visualizing probe may coexist in the cells, thus enabling an in vivo method of detecting and quantifying cGMP without disrupting the cells.

Further, in the method of detecting and measuring cGMP by the invention of the present application, a polynucleotide expressing the cGMP-visualizing probe may be introduced into cells, and by ontogenesis, the non-human animal totipotent cells may be generated into an individual non-human animal, for the cGMP-visualizing probe to coexist with cGMP in every cell of the resultant animal or its offspring.

Using the various methods described above, a transgenic non-human animal having the cGMP-visualizing probe and cGMP coexisting in every cell thereof maybe obtained in the invention of the present application by introducing a polynucleotide expressing the cGMP-visualizing probe into cells and developing the non-human animal totipotent cells into an individual. The transgenic non-human animal may be created by known preparative methods (for example, Proc. Natl. Acad. Sci. USA 77:7380–7384, 1980). The transgenic non-human animal obtained would have the cGMP-visualizing probe in every somatic cell, and may be used, for example, in the screening of various substances by introducing test substances such as pharmaceutical preparations or toxins to the body of said transgenic animal and measuring the concentration of cGMP in the cells and tissues.

Hereinafter, the present invention is described in more detail by reference to the Examples and the accompanying drawings. As a matter of course, the invention is not limited to the following examples, and various embodiments are possible.

The cGMP-visualizing probe of the invention of the present application is genetically encoded; thus it may be optimized by genetic engineering means. For example, the position of the cGMP-visualizing probe in the cell may be controlled by fusing it to a protein such as a signal sequence, guanylyl cyclase, a cyclic nucleotide-agonistic cation channel, and an anchoring protein for PKG Iα.

Further, similar- to the cGMP-visualizing probe of the invention of the present application, cyclic adenosine-phosphate (cAMP) visualizing probes may be developed based on knowledge on genetic engineering in relation to the binding domains of cyclic nucleotides.

EXAMPLES

Example 1

Preparation of cGMP-visualizing Probes

As shown in FIG. 1, cyan fluorescent protein (ECFP: F64L/S65T/Y66W/N1461/M153T/V163A/N212K) and yellow fluorescent protein (EYFP: S65G/V68L/Q69K/S72A/T203Y), which are mutants of green fluorescent protein (EGFP: for example, Current Biology 6(2), 178–182, 1996) derived from fluorescent Aequorea Victoria, were linked respectively to the N- and C-terminals of cGMP-dependent protein kinase (PKG Iα) by genetic engineering, to prepare a CFP-PKG Iα-YFP fusion protein (referred to hereinafter as CGY).

Besides this CGY construct (CGY-FL) having the full-length amino acid sequence of PKG Iα, the following CGY constructs were prepared in an analogous method: a CGY construct (CGY-A12) wherein in the amino acids 1 to 47 in PKG Iα, all of leucine, isoleucine and cysteine residues were converted into alanine residues, and a CGY construct (CGY-Del1) that is PKG Iα (Δ1–47) wherein the amino acids 1 to 47 in PKG Iα were deleted.

Further, the following analogues of CGY-Del1 were prepared in an analogous manner; a construct (CGY-Del2) wherein the linker sequence (MDELKY) of SEQ ID NO: 1 was introduced between PKG Iα (Δ1–47) and ECFP, a construct (CGY-Del3) wherein the linker sequence (YPYDVPDYAN) of SEQ ID NO: 2 was introduced between PKG Iα (Δ1–47) and ECFP, and a construct (CGY-Del4) wherein the linker sequence (MDELKY) of SEQ ID NO: 1 was introduced between PKG Iα (Δ1–47) and ECFP and the linker sequence (YPYDVPDYAN) of SEQ ID NO: 2 was introduced between PKG Iα (Δ1–47) and EYFP.

Example 2

Introduction of the cGMP-visualizing Probes (CGY) Into Chinese Hamster Ovary Cells Chinese hamster ovary cells (CHO-K1) were cultured in Ham's F-12 medium supplemented with 10% fetal calf serum (FCS) at 37° C. in 5% $CO_2$.

The resulting CHO-K1 cells were transfected by Lipofect AMINE 2000 reagent (Life Technologies) with CGY-FL, CGY-Del1 and CGY-A12 expression vectors respectively.

Within 12 to 24 hours after the transfection, the CHO-K1 cells expressing each CGY were removed and spread onto glass-bottom culture dishes.

Example 3

Imaging of CHO-K1 Into which the cGMP-visualizing Probes (CGY) Had Been Introduced First, the culture liquid in Example 2 was replaced with Hank's balanced salt solution.

Within 3 to 5 days after transfection with each type of CGY, the CHO-K1 cells were imaged at room temperature on a Carl Zeiss Axiovert 135 microscope with a cooled CCD camera MicroMAX (Roper Scientific Inc.) controlled by MetaFluor (Universal Imaging) The exposure time at 440±10 nm excitation was 50 ms. The fluorescence images were obtained through 480±15 nm and 535±12.5 nm filters with a 40×oil-immersion objective (Carl Zeiss).

Figure 2:
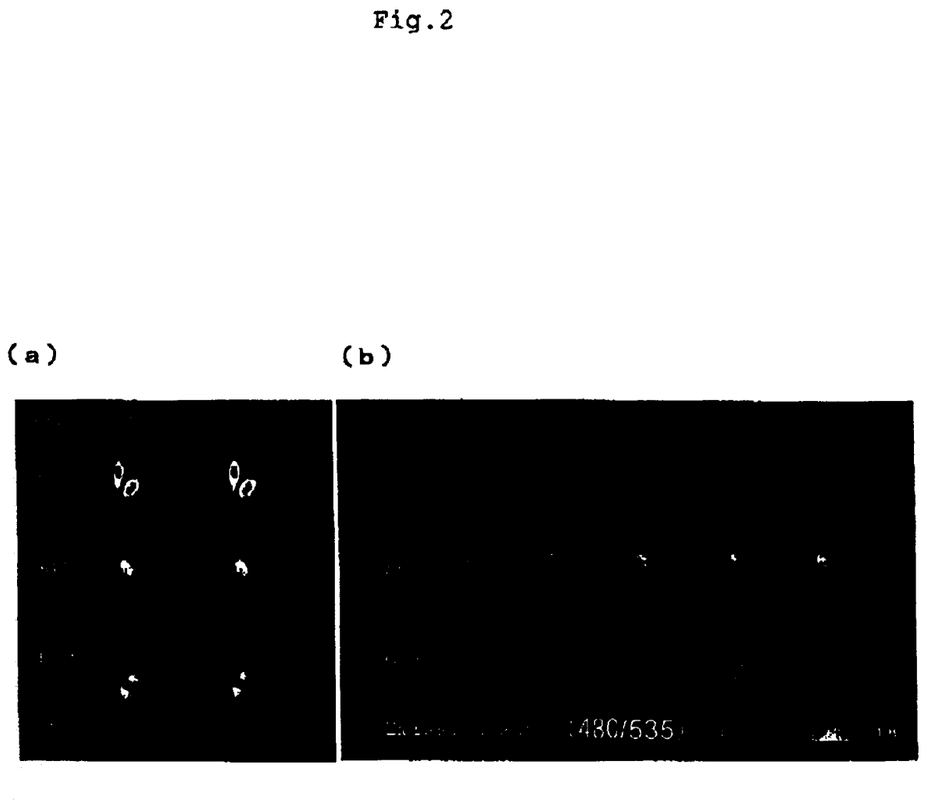
FIG. 2 shows the response to 8-Br-cGMP in CHO-K1 cells expressing the cGMP-visualizing probes for the Examples of the present invention, (a) is a microphotograph of the cells expressing CGY-FL, CGY-A12 and CGY-Del1 (excitation: 440±10 nm, filter: 480±15 nm (CFP) and 535±12.5 nm (YFP)). (b) shows the change in emission ratios at 480±15 nm to 535±12.5 nm with time for the CGY-expressing CHO-K1 cells coexisting with 1 mM 8-Br-cGMP.

FIG. 2(a) shows a microphotograph of CFP (480 nm) and YFP (535 nm) of the transfected cells. From this result, it was revealed that CGY-A12 was introduced into the cell nucleus.

Since about 30% of CHO-K1 cells expressing CGY-Del1 showed CFP and YFP fluorescence in the cell nucleus, the leucine/isoleucine zipper motif in the dimerization domain of PKG Iα may provide important information to the direct localization of kinase in the extranuclear compartment.

Example 4

Responses of the cGMP-visualizing Probes (CGY)

The CGY-expressing CHO-K1 cells prepared in Example 1 were stimulated with 8-Br-cGMP known as a cell membrane-permeable and phosphodiesterase-resistant-analogue of cGMP, and the fluorescence was measured under a fluorescence microscope.

(1) CGY-FL-expressing CHO-K1

FIG. 2(b) shows changes in emission ratios (480±15 nm to 535±12.5 nm) in the CGY-expressing CHO-K1 before and after the addition of 8-Br-cGMP (1 mM).

Figure 3:
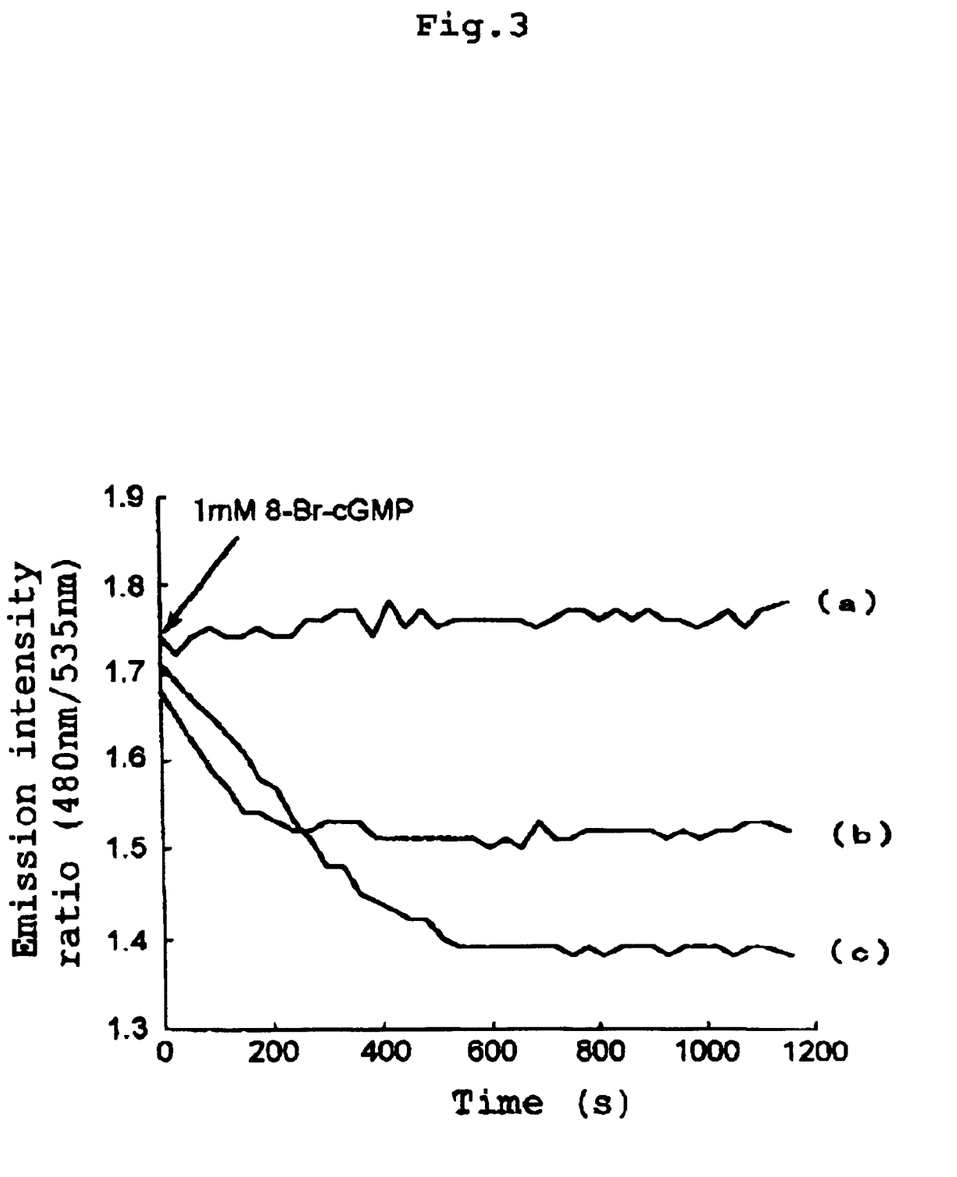
FIG. 3 is a graph showing the change with time in emission ratios upon stimulation of CGY-FL-, CGY-Del1- and CGY-A12-expressing CHO-K1 cells with 8-Br-cGMP for the Examples of the present invention. (a) is for CGY-FL, (b) for CGY-Del1, and (c) for CGY-A12 respectively.

Further, FIG. 3 shows changes with time in emission ratios in the cell substrate.

From these results, it was revealed that there is no significant emission ratio change of CGY-FL. It was also revealed that the fluorescence intensities of CFP and YFP were not affected by the addition of 8-Br-cGMP.

(2) CGY-Del1-expressing CHO-K1

On the other hand, a significant decrease in the emission ratio for the CGY-Del1-expressing CHO-K1 upon addition of 8-Br-cGMP was confirmed as shown in FIG. 2b.

Figure 4:
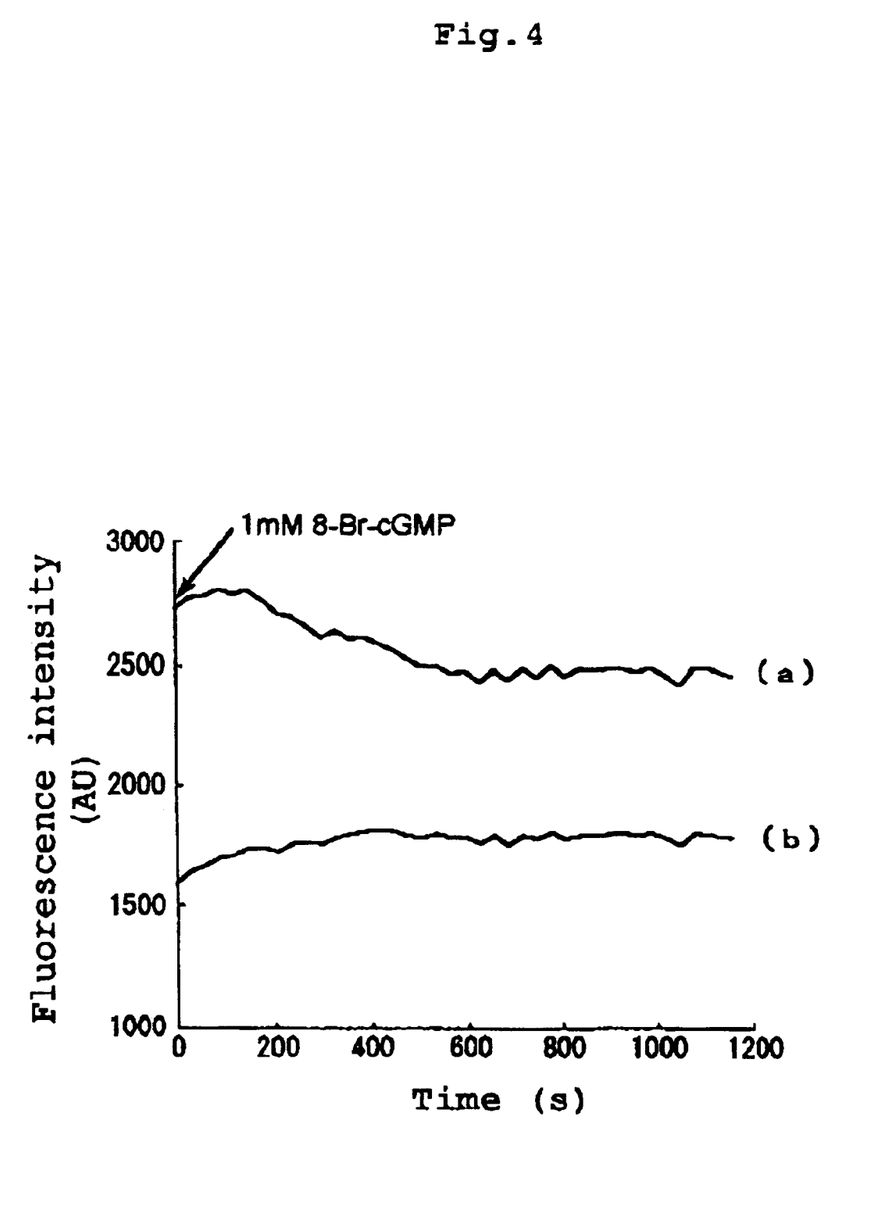
FIG. 4 is a graph showing the kinetic behavior of the cytoplasmic fluorescence intensity of CGY-Del1-expressing CHO-K1 cells at 480±15 nm (CFP) and 535±12.5 nm (YFP) for the Examples of the present invention. (a) is for CFP, and (b) for YFP respectively.

Further, as shown in FIG. 4, reciprocal changes in CFP and YFP fluorescence intensities were observed. Further, it was found that the decrease in the emission ratios has the same tendency with time as for the reciprocal changes in CFP and YFP fluorescence intensities.

These results indicate that the fluorescence resonance energy transfer (FRET) between CFP and YFP increases upon binding of 8-BR-cGMP to CGY-Del1.

(3) CGY-A12-expressing CHO-K1

In CGY-A12-expressing CHO-K1 cells, a change in the emission was observed by the addition of 8-Br-cGMP (FIGS. 2b, 3). However, the maximum change in this emission ratio was as small as one-third of that for CGY-Del1.

Example 5

Influence of Introduction of the Linker Sequences into the cGMP-visualizing Probes CGY-Del1, CGY-Del2, CGY-Del3 and CGY-Del4 prepared in Example 1 were expressed in CHO-K1 cells in the same manner as in Example 2, and examined for changes in the emission intensities.

Figure 5:
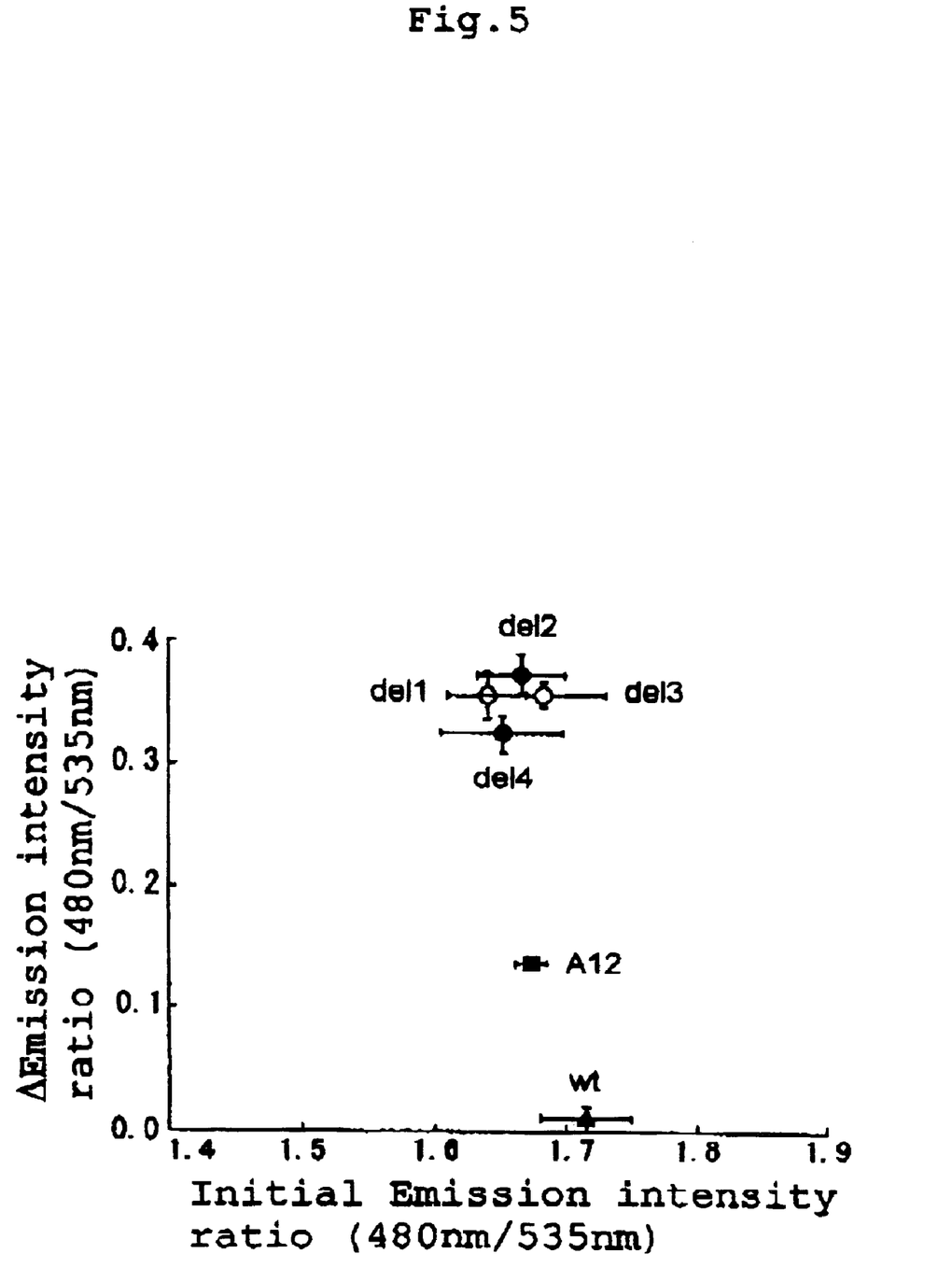
FIG. 5 is a graph showing initial emission ratios and changes in the emission ratios for CGY-FL, CGY-A12, CGY-Del1, CGY-Del2, CGY-Del3, and CGY-Del4 in the Examples of this invention.

The relationship between the initial emission ratio and the change in the emission ratio upon coexistence with 8-Br-cGMP is shown in FIG. 5.

From this result, the responses of cGMP-expressing CHO-K1 cells to addition of 8-Br-cGMP were confirmed, but it was revealed that the linker sequences SEQ ID NO:NO. 1 (MDELKY) and SEQ ID NO: 2 (YPYDVPDYAN) both showed no significant effect on either the initial emission ratio or the emission ratio.

No significant difference in the initial emission ratio was observed between CGY-A12 and COY-DEL 1 to 4; therefore, it is suggested that introducing various flexible domains into the polypeptide chain may optimize the structure of the cGMP-visualizing probe of the present invention.

These results indicate that CGY-Del 1 to 4 are preferable as the cGMP-visualizing probes for measuring intracellular cGMP levels.

Example 6

Introduction of CGY Into Human Embryonic Kidney Cells

Human embryonic kidney cells (HEK293) were cultured in Dulbecco's modified eagle medium supplemented with 10% FCS, 1 mM sodium pyruvate, and 0.1 mM nonessential amino acids at 37° C. in 5% $CO_2$, to give HEK293 cells.

The resulting HEK293 cells were transfected by the same method as in Example 2 with CGY-Del1, CGY-Del2, CGY-Del3 and CGY-Del4 expression vectors, to give HEK293 cells expressing each type of CGY.

Example 7

Quantification of cGMP in the Living Cells by the cGMP-visualizing Probes

The cGMP-visualizing probes were used to detect intracellular cGMP generated upon stimulation of the living cells with nitrogen monoxide (NO).

First, to activate the soluble guanylyl cyclase in the HEK293 cells having CGY-Del1 introduced therein obtained in Example 6, NOC-7, a compound for releasing NO spontaneously in a rate-controlled manner, was added to give its final extracellular concentration of 500 µM.

Figure 6:
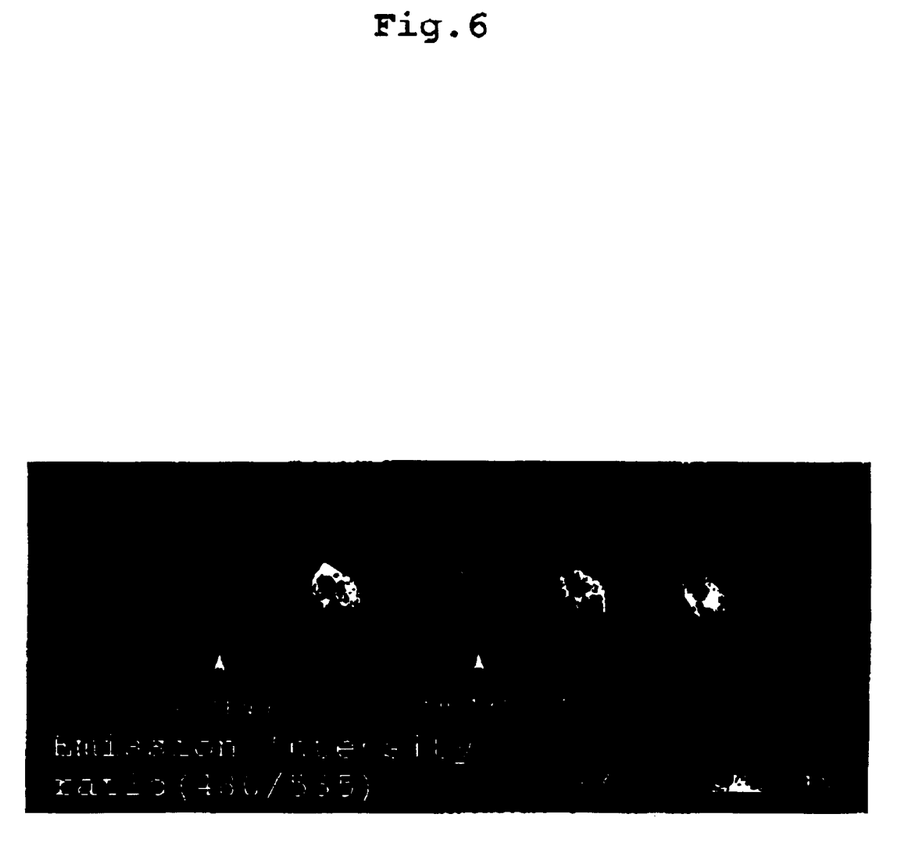
FIG. 6 shows the cytoplasmic emission ratios upon stimulation of CGY-Del1-expressing HEK293 cells with 500 μM of NOC-7 for the Examples of the present invention (-Br-cGMP added 900 seconds after addition of NOC-7 8.)

FIG. 6 shows a photomicrograph of emissions induced by NOC-7 in the CGY-Del1-expressing HEK293 single cell.

FIG. 6 indicates that the emission ratio was rapidly decreased upon addition of 500 µM NOC-7 to the CGY-Del1-expressing HEK293 cells, and a subsequent increase in the emission ratio to nearly the initial level was observed.

Figure 7:
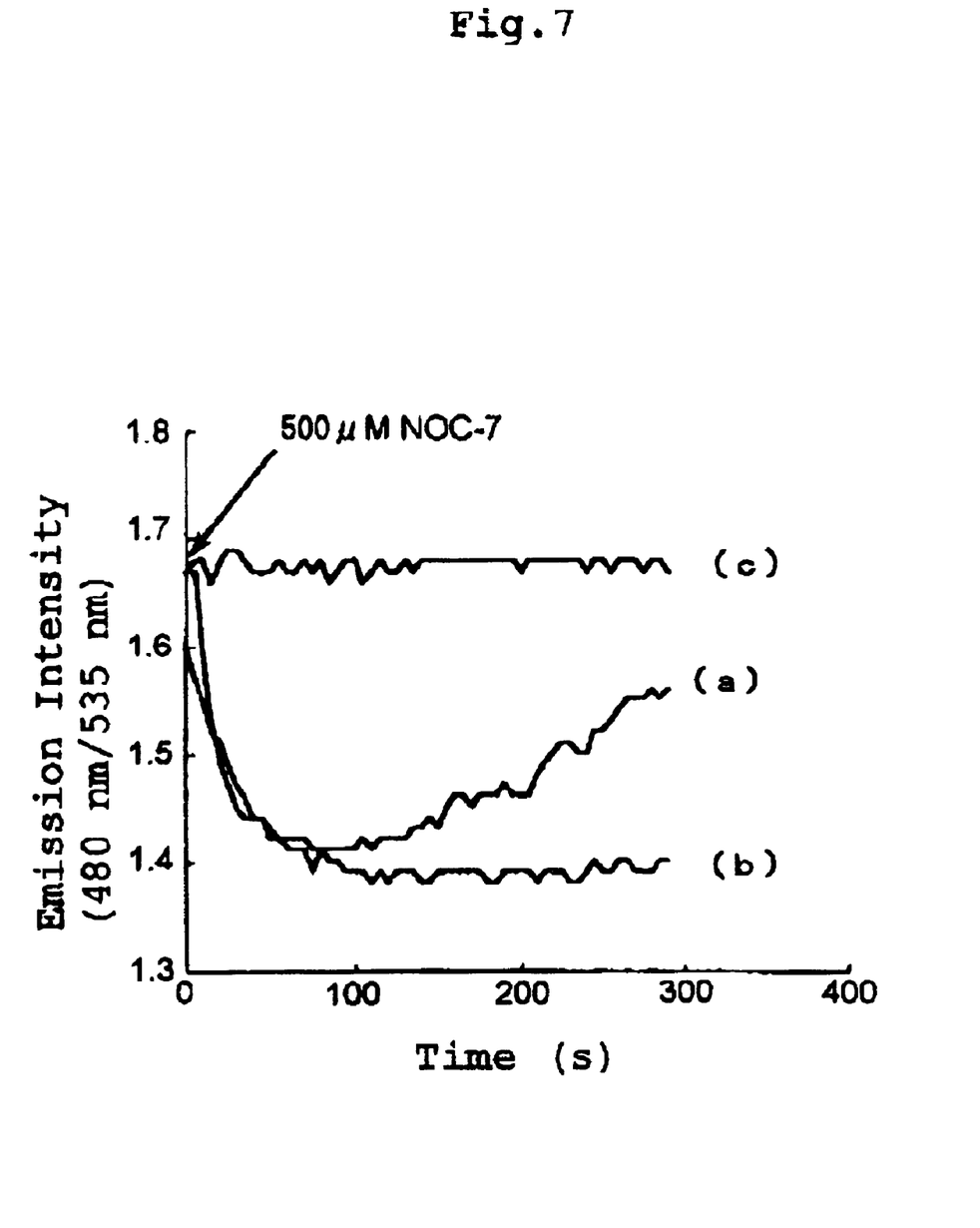
FIG. 7 is a graph showing the changes in emission ratios upon stimulation of CGY-Del1-expressing HEK293 cells with 500 μM NOC-7 for the Examples of the present invention. (a) shows CGY-Del1-expressing HEK293 cells, (b) shows CCY-Del1-expressing HEK293 cells treated with 100 μM zaprinast, and (c) CGY-Del1-expressing HEK293 cells treated with 10 μM ODQ.

FIG. 7 shows changes in the NOC-7-induced emission ratio for the CGY-Del1-expressing HEK293 single cell.

The emission ratio was first rapidly decreased followed by a slower increase in the ratio.

Then, when the CGY-Del1-expressing HEK293 cells were treated with 100 µM zaprinast (selective inhibitor for cGMP-specific phosphodiesterase), the same initial rapid decrease in the emission ratio was observed. However, the later slower increase in the emission ratio was not observed.

When the cells were pre-treated with 10 µM ODQ (selective inhibitor for NO-sensitive guanylyl cyclase), the change in the emission ratio elicited by NOC-7 was not observed.

From FIG. 7, it was suggested that the decrease in the emission ratio followed by an increase in the ratio is attributable to decomposition of cGMP by cGMP-specific phosphodiesterase.

Similar results were also obtained by using the HEK293 cells expressing CGY-DEI 2 to 4.

From the above results, it was revealed that the occurrence of cGMP in living cells could be confirmed by using the cGMP-visualizing probes of the invention of the present application.

Example 8

Measurement of Intracellular cGMP by the cGMP-visualizing Probe

Accordingly, 1 mM 8-Br-cGMP, a phosphodiesterase-resistant analogue of cGMP, was added to the system described above.

Figure 8:
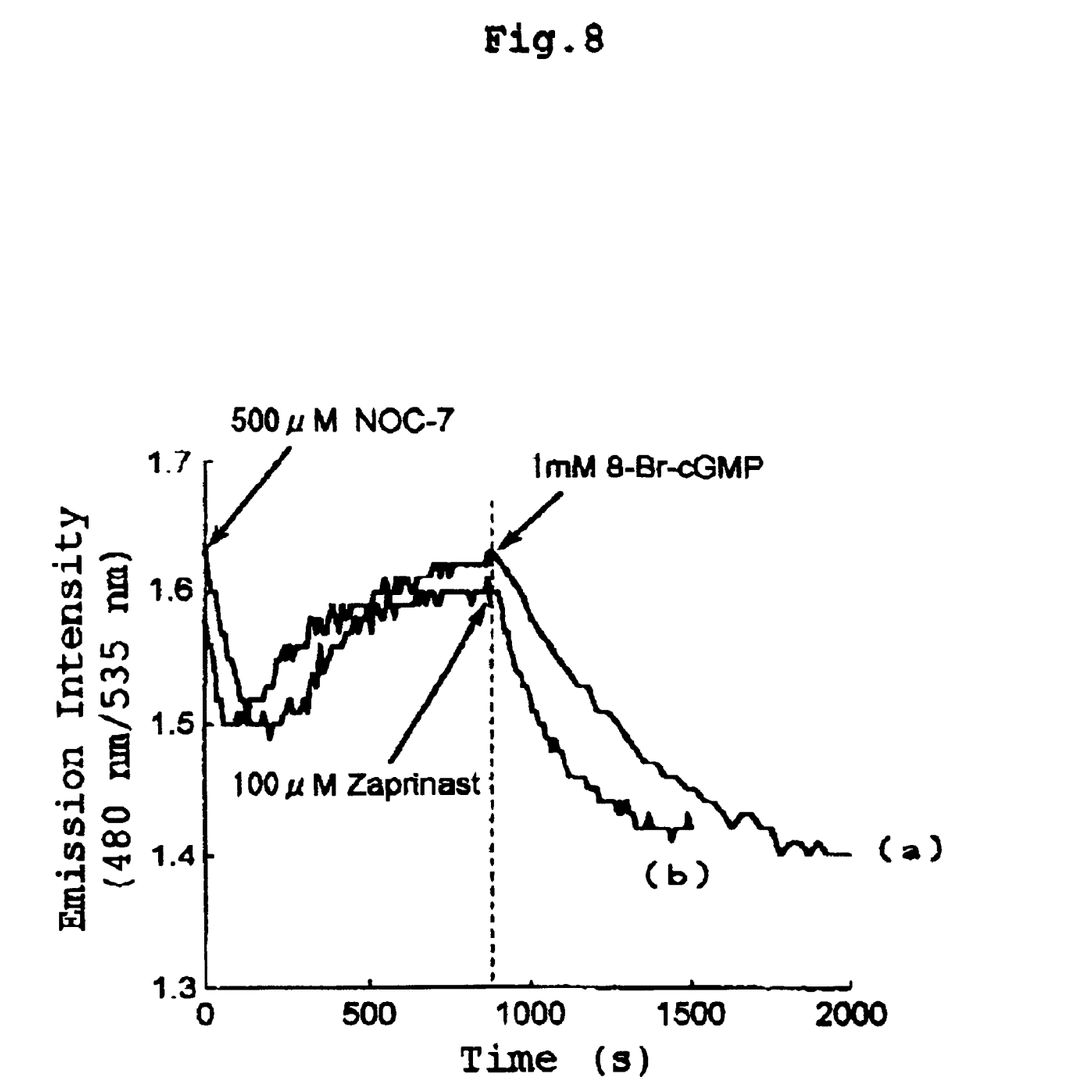
FIG. 8 is a graph showing changes in the emission ratios upon stimulation of CGY-Del1-expressing HEK293 cells with 500 μM of NOC-7 in the Examples of this invention. (a) 8-Br-cGMP added 900 seconds after addition of NOC-7; (b) zaprinast added 900 seconds after addition of NOC-7.

The results are shown in FIG. 8.

Following a decrease and a subsequent increase in the emission ratio, the ratio was decreased again by adding 1 mM 8-Br-cGMP. By using zaprinast in place of 8-Br-cGMP, a similar re-increase was confirmed in the system where the emission ratio was recovered.

From the foregoing results, it was confirmed that the response of CGY-Del1 in detecting cGMP is reversible, and by using the cGMP-visualizing probe of the invention of the present application, the fluctuating concentration of cGMP in living cells can be measured.

INDUSTRIAL APPLICABILITY

As described in detail above, the present invention provides a cGMP-visualizingprobe that enables the easy detection and quantification of cGMP with high accurately even in vivo, as well as a method of detecting and quantifying cGMP by using the same.

What is claimed is:

1. A cGMP-visualizing probe, comprising:
a polypeptide that binds specifically to cGMP, wherein the polypeptide is obtained by deleting amino acids 1 to 47 of cGMP-dependent protein kinase Iα (PKG Iα); and
two chromophores with different fluorescence wavelengths, one of which is linked to the N-terminal and the other of which is linked to the C-terminal of the polypeptide, wherein the chromophores are capable of exhibiting fluorescence resonance energy transfer (FRET).

2. The cGMP-visualizing probe of claim 1, wherein the chromophores are cyan fluorescent protein linked to the N-terminal of the polypeptide and yellow fluorescent protein linked to the C-terminal of the polypeptide.

3. A method for detecting and quantifying cGMP, which comprises:
making the cGMP-visualizing probe of claim 1 coexist with cGMP; and
measuring the change in the fluorescence wavelength.

* * * * *